United States Patent
Kumar et al.

(10) Patent No.: US 11,197,838 B2
(45) Date of Patent: Dec. 14, 2021

(54) INFUSION DOSAGE FORM OF NOREPINEPHRINE

(71) Applicant: SUN PHARMACEUTICAL INDUSTRIES LIMITED, Maharashtra (IN)

(72) Inventors: Samarth Kumar, Baroda (IN); Maheshkumar Parasmal Soni, Baroda (IN); Praveen Kumar Srivastava, Baroda (IN); Prashant Kane, Baroda (IN); Subhas Balaram Bhowmick, Baroda (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 16/989,027

(22) Filed: Aug. 10, 2020

(65) Prior Publication Data

US 2021/0038539 A1  Feb. 11, 2021

(30) Foreign Application Priority Data

Aug. 8, 2019 (IN) .............. 201921032096

(51) Int. Cl.
| | | |
|---|---|---|
| *A61K 31/137* | (2006.01) | |
| *A61K 9/08* | (2006.01) | |
| *A61K 47/02* | (2006.01) | |
| *A61K 47/18* | (2017.01) | |
| *A61K 9/00* | (2006.01) | |

(52) U.S. Cl.
CPC .............. *A61K 31/137* (2013.01); *A61K 9/08* (2013.01); *A61K 47/02* (2013.01); *A61K 47/183* (2013.01); *A61K 9/0019* (2013.01)

(58) Field of Classification Search
CPC ........ A61K 31/137; A61K 9/08; A61K 47/02; A61K 47/183; A61K 9/0019
See application file for complete search history.

(56) References Cited

U.S. PATENT DOCUMENTS

| | | | |
|---|---|---|---|
| 9,119,876 B1 * | 9/2015 | Kannan .................. | A61K 47/18 |
| 2011/0003015 A1 * | 1/2011 | Baillie .................. | A61K 33/04 |
| | | | 424/711 |
| 2016/0058715 A1 * | 3/2016 | Rakesh .................. | A61K 31/00 |
| | | | 514/653 |

OTHER PUBLICATIONS

Labthink, 2012 (Year: 2012).*
Duplex® Package Insert, 2009 (Year: 2009).*
Hans Aaron Bates, "Characterization of Tetrahydroisoquinolines Produced by Pictet-Spengler Reactions of Norepinephrine with Formaldehyde and Acetaldehyde", Journal of Organic Chemistry, vol. 48, Issue: 11, pp. 1932-1934, Journal, 1983.
Zhang Cui-ying et al., "Advance of Pharmacological Studies on Protocatechuic Aldehyde China Academy of Chinese Medical Sciences", Chinese Journal of Experimental Traditional Medical Formulae.
Anonymous, "Noradrenaline Infusion", Medsafe.Govt.NZ, Oct. 1, 2010, pp. 1-7.
International Application No. PCT/IB2020/057517, International Search Report and Written Opinion dated Nov. 12, 2020, 12 pages.

* cited by examiner

*Primary Examiner* — Snigdha Maewall

(74) *Attorney, Agent, or Firm* — Blank Rome LLP

(57) ABSTRACT

The present invention provides a ready to use stable aqueous dosage form of norepinephrine comprising an aqueous solution of norepinephrine or its pharmaceutically acceptable salt, one or more sulfite antioxidants and an ion chelator. The present invention also provides an infusion container filled with an aqueous solution of norepinephrine or its pharmaceutically acceptable salt, wherein the said solution is stable for a prolonged period of time and can be terminally sterilized by autoclaving.

25 Claims, No Drawings

INFUSION DOSAGE FORM OF NOREPINEPHRINE

CROSS REFERENCE

The present patent application claims priority from Indian Provisional Patent Application No. 201921032096 filed on Aug. 8, 2019.

FIELD OF THE INVENTION

The present invention relates to an infusion container filled with an aqueous solution of norepinephrine or its pharmaceutically acceptable salt, wherein the said solution is stable and can be terminally sterilized by autoclaving. The present invention also relates to a method for preparation of a stable autoclavable dosage form of norepinephrine.

BACKGROUND OF THE INVENTION

Norepinephrine is a sympathomimetic amine, which functions as a peripheral vasoconstrictor and as an inotropic stimulator of the heart and dilator of coronary arteries. It is also known as l-arterenol, levarterenol or l-norepinephrine or noradrenaline. Norepinephrine bitartrate, a catecholamine has the following structural formula:

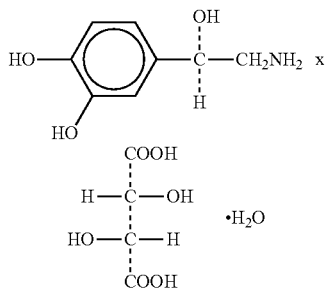

Norepinephrine (NE) is administered by intravenous infusion for blood pressure control in certain acute hypotensive states e.g., pheochromocytomectomy, sympathectomy, poliomyelitis, spinal anesthesia, myocardial infarction, septicemia, blood transfusion, and drug reactions. It is also used as an adjunct in the treatment of cardiac arrest and profound hypotension.

Levophed® and other metabisulfites containing norepinephrine products are available as preconcentrate solutions having a norepinephrine concentration of 4 mg/4 ml. The 4 mg/4 ml preconcentrate solution of norepinephrine needs to be diluted with 1,000 mL of a 5% dextrose containing solution before administration. The step of dilution or handling before administration can lead to medication or handling errors. Also, there are chances of contamination of the infusion solution, which can be lead to severe adverse effects.

To date, there has been no report of a ready-to-infuse dosage form of norepinephrine that is terminally sterilized by autoclaving which is the most preferred method of sterilization for parenteral dosage forms and yet chemically stable and robust. Thus, there is an urgent need for a stable, autoclavable, ready-to-infuse dosage form of norepinephrine which comprises norepinephrine at lower concentration suitable for direct administration to the patient and at the same time which remains stable upon autoclaving and upon long-term storage. To achieve this objective, the present inventors have attempted several trials and have arrived at a unique combination of antioxidant and ion chelator which provided a dosage form that is stable and robust. Particularly during such attempts, it was observed that solution of norepinephrine in the diluted form is more prone to degradation compared to a concentrated solution. For instance, dilute solution of norepinephrine having a concentration of about 4 microgram/ml to about 75 microgram/ml when subjected to autoclaving resulted in generation of higher level of impurities compared to solution having 1000 microgram/ml of norepinephrine. Therefore, it was indeed a challenge to develop a dilute, ready-to-administer aqueous solution of norepinephrine which is stable and robust. The inventors found that upon autoclaving of such dilute solutions, following impurities were generated:

1) 1,2,3,4-tetrahydroisoquinoline-4,6,7-triol (THIQ), impurity of Formula I,

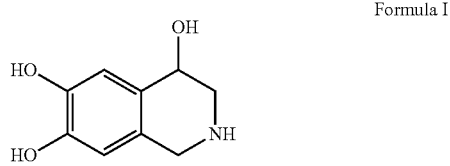 [SMILES: Oc1cc2c(cc1O)C(O)CNC2]

Formula I 2) 1,2,3,4-tetrahydroisoquinoline-4,7,8-triol (THIQ-1), impurity of Formula II, and

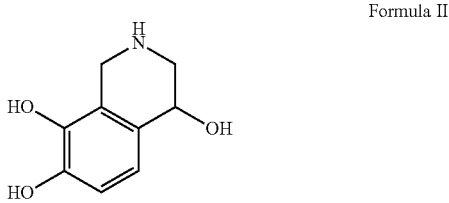 [SMILES: Oc1ccc2c(c1O)CNCC2O]

Formula II 3) 3, 4 dihydroxybenzaldehyde (DBA), impurity of Formula III

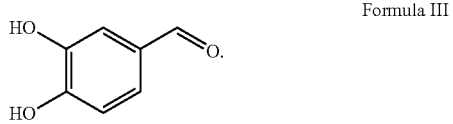

Formula III

Out of these impurities, 3, 4 dihydroxybenzaldehyde, (impurity of Formula III) is known to be undesirable. It has been reported that 3, 4 dihydroxybenzaldehyde, a protocatechuic aldehyde is toxic to the heart as well extensive pharmacological activities such as antiatherosclerosis, cardiomyocyte protection, anti-thrombotic, neuroprotection etc., which are unintended, undesired effects of norepinephrine as reported in ZHANG Cui-ying et al, "Advance of Pharmacological Studies on Protocatechuic Aldehyde China Academy of Chinese Medical Sciences", Chinese Journal of Experimental Traditional Medical Formulae. It has also been reported that tetrahydroisoquinolines (such as impurity of Formula I) acts as false neurotransmitter which is undesirable as per abstract of Hans Aaron Bates, "Characterization of Tetrahydroisoquinolines Produced by Pictet-Spengler Reactions of Norepinephrine with Formaldehyde and Acetaldehyde", Journal of Organic Chemistry, Volume: 48, Issue: 11, Pages: 1932-4, Journal, 1983.

The present inventors discovered that generation of these impurities of Formula I, Formula II or Formula III are controlled using combination of stabilizers selected from antioxidants and an ion chelator. The present inventors thus arrived at a robust, stable, ready-to-infuse, aqueous solution of norepinephrine having a concentration of about 4 microgram/ml to about 75 microgram/ml, preferably about 10 microgram/ml to about 75 microgram/ml, contained in a flexible plastic infusion container that sustains application of heat and pressure during autoclaving and yet remains chemically stable.

SUMMARY OF THE INVENTION

The present invention provides a ready to infuse stable parenteral dosage form comprising:

a) an aqueous solution of norepinephrine or its pharmaceutically acceptable salt;

b) at least one sulfite antioxidant, and c) at least one ion chelator.

In another aspect, the present invention also provides a flexible infusion container comprising an aqueous solution of norepinephrine or its pharmaceutically acceptable salt, at least one stabilizer and an ion chelator.

In yet another aspect the present invention provides an autoclavable ready to infuse stable dosage form comprising an aqueous solution of norepinephrine or its pharmaceutically acceptable salt, with at least one stabilizer.

DESCRIPTION OF THE INVENTION

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

The present invention provides a ready to use stable aqueous dosage form of norepinephrine in a flexible infusion container comprising an aqueous solution of norepinephrine or its pharmaceutically acceptable salt with at least one sulfite antioxidants and at least one ion chelator/chelating agent. The said solution can be subjected to autoclaving and upon storage the solution contains substantially lower amount of impurity of Formula I, Formula II or Formula III, and a lesser amount of total impurity compared to the impurity levels present in the aqueous solution that is devoid of such components and is autoclaved.

In yet another embodiment the present invention provides a ready to use stable aqueous dosage form of norepinephrine in a flexible infusion container comprising an aqueous solution of norepinephrine or its pharmaceutically acceptable salt with at least one sulfite antioxidant selected from sodium sulfite, sodium bisulfite, sodium metabisulfite or potassium metabisulfite; and one or more ion chelator or chelating agent selected from ethylenediaminetetraacetic acid, edetic acid, disodium edetate dihydrate, disodium EDTA, Edetate Trisodium, Edetate Sodium, Edetate Calcium Disodium, Pentasodium Pentetate, di-potassium edetate, dipotassium EDTA, diethylenetriamine pentaacetic acid or mixture thereof and the like. The solution may optionally further comprise one or more other antioxidants selected from butylated hydroxyl anisole, ascorbic acid, sodium ascorbate, propyl gallate, vitamin E and/or alpha-tocopherol. The said solution is subjected to autoclaving, upon storage the solution contains substantially lower amount of impurity of Formula I, Formula II or Formula III and lesser amount of total impurity compared to the impurity levels present in the aqueous solution that is devoid of such components and is autoclaved.

In some embodiments a ready to use stable aqueous dosage form of norepinephrine in a flexible infusion container is provided, said container comprising an aqueous solution of norepinephrine or its pharmaceutically acceptable salt with at least one sulfite antioxidant selected from sodium sulfite, sodium bisulfite, sodium metabisulfite or potassium metabisulfite; and one or more ion chelator or chelating agent selected from ethylenediaminetetraacetic acid or its salts. The said solution may optionally further comprise one or more other antioxidants. The said solution is subjected to autoclaving, upon storage the solution contains substantially lower amount of impurity of Formula I, Formula II or Formula III and a lesser amount of total impurity compared to the impurity levels present in the aqueous solution that is devoid of such components and is autoclaved.

In other embodiment a ready to use stable aqueous dosage form of norepinephrine in a flexible infusion container is provided, said container comprising an aqueous solution comprising: norepinephrine or its pharmaceutically acceptable salt at a concentration equivalent to about 10 µg/ml to about 75 µg/ml of norepinephrine base, sodium metabisulfite at a concentration ranging from about 3 µg/ml to about 15 µg/ml, and an ion chelator ethylenediaminetetraacetic acid or its salts at a concentration ranging from about 4 µg/ml to about 100 µg/ml, wherein the said aqueous solution is filled in the container in volumes ranging from 100 ml to 1000 ml, and wherein the filled container when subjected to autoclaving and upon storage, the solution contains substantially lower amount of impurity of Formula I, Formula II or Formula III, compared to the impurity levels present in the aqueous solution that is devoid of sodium metabisulfite and/or ethylenediaminetetraacetic acid or its salts and mixture thereof.

In another embodiment a ready to use stable aqueous dosage form of norepinephrine in a flexible infusion container is provided, said container comprising an aqueous solution comprising: norepinephrine or its pharmaceutically acceptable salt at a concentration equivalent to about 10 µg/ml to about 75 µg/ml of norepinephrine base, sodium metabisulfite at a concentration ranging from about 3 µg/ml to about 15 µg/ml, butylated hydroxyl anisole, at a concentration ranging from about 0.1 microgram/ml to about 0.4 microgram/ml, and an ion chelator ethylenediaminetetraacetic acid or its salts at a concentration ranging from about 4 μg/ml to about 100 μg/ml, wherein the said aqueous solution is filled in the container in volumes ranging from 100 ml to 1000 ml, and wherein the filled container when subjected to autoclaving and upon storage, the solution contains substantially lower amount of impurity of Formula I, Formula II or Formula III, compared to the impurity levels present in the aqueous solution that is devoid of sodium metabisulfite and ethylenediaminetetraacetic acid or its salts and mixture thereof.

In other embodiment a stable ready to use aqueous solution of Norepinephrine in an infusion bag, said bag comprising 0.016-0.064 mg/mL base of norepinephrine, with a suitable osmogen solution, with sodium metabisulfite and butylated hydroxyanisole as antioxidants and Disodium Edetate, wherein the pH of the solution has been adjusted between 3.0 to 4.5 with sodium hydroxide or hydrochloric acid and the air in the infusion bags has been displaced by an inert gas such as nitrogen gas.

In yet another embodiment the present invention provides a ready to infuse parenteral dosage form stable at room temperature comprising an infusion container comprising an aqueous solution of norepinephrine or its pharmaceutical acceptable salt with at least one sulfite antioxidant and at least one ion chelator.

In a further embodiment, the present invention provides a ready to infuse stable parenteral dosage form comprising an aqueous solution of norepinephrine or its pharmaceutically acceptable salt; at least one sulfite antioxidant; and at least one ion chelator.

In another embodiment, the present invention provides a ready to infuse stable parenteral dosage form comprising: an aqueous solution of norepinephrine or its pharmaceutically acceptable salt; stabilizers comprising at least one sulfite antioxidant; and at least one ion chelator.

The term 'stable' as used herein means that the solution of norepinephrine in the dosage form upon autoclaving is physically as well as chemically stable when the dosage form is stored at room temperature (about 25° C.) for at least 6 months, preferably for at least 12 months and more preferably at least 18 months. Suitably, the solution of norepinephrine remains physically stable, with no precipitation or crystallization or color change upon storage and has shelf life period of about 18 months or longer when stored at room temperature. Suitably, the solution of norepinephrine remains chemically stable when stored at room temperature (about 25° C.) and at refrigerated conditions (2-8° C.), wherein various parameters such as the drug content (assay of norepinephrine) and content of related substances, i.e. known and unknown impurities remains within specified limits, upon storage for prolonged period of time such as for at least 12 months, preferably for 18 months, more preferably 24 months or longer. Suitably, the value of assay of norepinephrine remains within the specified limit of 90-115% by weight or there occurs not more than 5% drop in the content of norepinephrine of the label claim; the highest unknown impurity remains within the specified limit of not more than 0.2%; the known Impurities of Formula I, Formula II or Formula III remains within the specified limit of not more than 0.2% and the total impurities remain below 2.0%, preferably below 1.0%.

The term 'stable' also means that the solution of norepinephrine upon autoclaving and upon storage at 40° C./25% relative humidity for a period of at least 3 months, preferable for a period of at least 6 months, remains physically and chemically stable such that the content of known impurity of Formula I, Formula II or Formula III remains not more than 0.2% by weight of norepinephrine, and the content of total impurities remains not more than 1.0% by weight of norepinephrine and there occurs not more than 5% drop in the content of norepinephrine.

In some embodiments, the content of impurities of Formula I, Formula II or Formula III remains not more than 0.1% by weight of norepinephrine and/or the content of total impurities remains not more than 1.0% by weight of norepinephrine, upon autoclaving and also, there occurs no more than 5% drop in the content of norepinephrine during any of the stages of preparation and during storage of the dosage form at room temperature for a period of at least 18 months or at 40° C./25% relative humidity for a period of at least 6 months.

The impurity of Formula I is 1,2,3,4-tetrahydroisoquinoline-4,6,7-triol (THIQ) and is represented by the following structure:

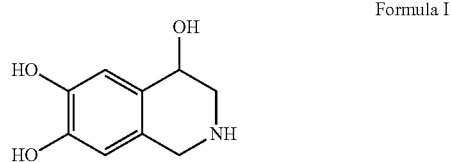 [SMILES: Oc1cc2c(cc1O)C(O)CNC2]

Formula I

The impurity of Formula II is 1,2,3,4-tetrahydroisoquinoline-4,7,8-triol (THIQ-1) and is represented by the following structure:

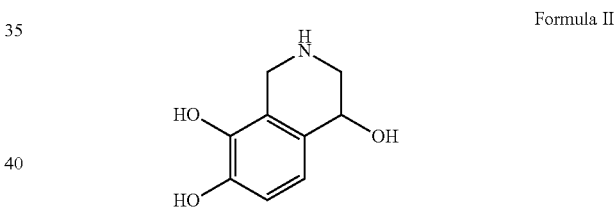

Formula II

The impurity of Formula III is 3,4-dihydroxybenzaldehyde (DBA) and is represented by the following structure:

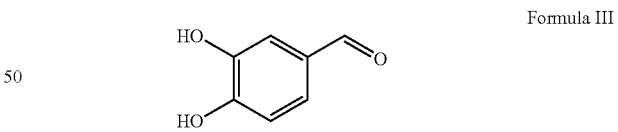

Formula III

In yet another embodiment the present invention provides a flexible infusion container comprising an aqueous solution of norepinephrine or its pharmaceutically acceptable salt present at a concentration ranging from about 4 microgram/ml to about 75 microgram/ml equivalent of norepinephrine base, preferably at a concentration ranging from about 10 microgram/ml to about 75 microgram/ml equivalent of norepinephrine base and at least one stabilizer comprising sodium metabisulfite at a concentration ranging from about 3 microgram/ml to about 15 microgram/ml and ethylenediaminetetraacetic acid or its salts at a concentration ranging from about 4 microgram/ml to about 100 microgram/ml, wherein the aqueous solution is filled in the container in volumes ranging from about 100 ml to about 1000 ml, in some further embodiments, about 100 to about 500 ml, said filled container when subjected to autoclaving and/or upon storage, the solution contains substantially lower amount of either one or more of the impurities of Formula I, Formula II or Formula III, compared to the impurity levels present in the aqueous solution that is free of sodium metabisulfite and/or ethylenediaminetetraacetic acid or its salts.

In a preferred one aspect of the invention, the pharmaceutically acceptable salt of norepinephrine is norepinephrine bitartrate, and is present in the solution at a concentration of about 16 microgram/ml to about 64 microgram/ml, equivalent to norepinephrine base. In yet another aspect of the invention, sodium metabisulfite is present at a concentration ranging from about 3.2 microgram/ml to about 12.8 microgram/ml. In yet another aspect of the invention, ethylenediaminetetraacetic acid or its salt is present at a concentration ranging from about 10 microgram/ml to about 75 microgram/ml, preferably at a concentration ranging from about 16 microgram/ml to about 64 microgram/ml. In yet another aspect of the invention, the aqueous solution optionally comprises butylated hydroxyl anisole which is present at a concentration ranging from about 0.1 microgram/ml to about 0.4 microgram/ml. In yet another aspect of the invention, the solution is free of sugar and/or sugar alcohol.

In a further embodiment, the present invention provides a flexible infusion container comprising an aqueous solution comprising:
(i) norepinephrine or its pharmaceutically acceptable salt at a concentration equivalent to about 10 microgram/ml to about 75 microgram/ml of norepinephrine base,
(ii) at least one stabilizer comprising sodium metabisulfite at a concentration ranging from about 3 microgram/ml to about 15 microgram/ml and ethylenediaminetetraacetic acid or its salts at a concentration ranging from about 4 microgram/ml to about 100 microgram/ml,
(iii) the aqueous solution is filled in the container in volumes ranging from about 100 ml to about 1000 ml, and
the filled container when subjected to autoclaving and upon storage, the solution contains substantially lower amount of either one or more of the impurities of Formula I, Formula II or Formula III, compared to the impurity levels present in the aqueous solution that is devoid of sodium metabisulfite and ethylenediaminetetraacetic acid or its salts and mixture thereof.

In a further embodiment, the present invention provides a flexible infusion container comprising an aqueous solution comprising:
(i) norepinephrine or its pharmaceutically acceptable salt at a concentration equivalent to about 10 microgram/ml to about 75 microgram/ml of norepinephrine base,
(ii) at least one stabilizer comprising sodium metabisulfite at a concentration ranging from about 3 microgram/ml to about 15 microgram/ml, butylated hydroxyl anisole at a concentration ranging from about 0.1 microgram/ml to about 0.4 microgram/ml, and ethylenediaminetetraacetic acid or its salts at a concentration ranging from about 4 microgram/ml to about 100 microgram/ml,
(iii) the aqueous solution is filled in the container in volumes ranging from about 100 ml to about 1000 ml, and
the filled container when subjected to autoclaving and upon storage, the solution contains substantially lower amount of either one or more impurities of Formula I, Formula II or Formula III, compared to the impurity levels present in the aqueous solution that is devoid of sodium metabisulfite or ethylenediaminetetraacetic acid or its salts and mixture thereof.

In another embodiment, the present invention provides an infusion container filled with an aqueous solution of norepinephrine, the solution consisting essentially of
(i) norepinephrine or its pharmaceutically acceptable salt at a concentration equivalent to about 16.0 microgram/ml to about 64.0 microgram/ml of norepinephrine base,
(ii) sodium metabisulfite at a concentration ranging from about 3 microgram/ml to about 15 microgram/ml,
(iii) ethylenediaminetetraacetic acid or its salt at a concentration ranging from about 4 microgram/ml to about 100 microgram/ml,
(iv) sodium chloride,
(v) pH adjusting agent,
(vi) solution having a pH in the range of 3.0 to 4.5, and
wherein the solution filled in the infusion container is terminally sterilized by autoclaving, and the solution upon autoclaving and subsequent storage at 40° C./25% relative humidity for a period of at least 6 months contains not more than 0.2% by weight of impurity of Formula I or not more than 0.2% by weight of impurity of Formula II or not more than 0.2% by weight of impurity of Formula III and not more than 1.0% by weight of total impurities, and the solution upon autoclaving and subsequent storage at 25° C./40% relative humidity for a period of at least 18 months contains not more than 0.2% by weight of impurity of Formula I or not more than 0.2% by weight of impurity of Formula II or not more than 0.2% by weight of impurity of Formula III and not more than 1.0% by weight of total impurity.

In some embodiment, the present invention provides an infusion container filled with an aqueous solution of norepinephrine, the solution consisting essentially of
(i) norepinephrine or its pharmaceutically acceptable salt at a concentration equivalent to about 16.0 microgram/ml to about 64.0 microgram/ml of norepinephrine base,
(ii) sodium metabisulfite at a concentration ranging from about 3 microgram/ml to about 15 microgram/ml,
(iii) butylated hydroxyl anisole at a concentration ranging from about 0.1 microgram/ml to about 0.4 microgram/ml,
(iv) ethylenediaminetetraacetic acid or its salt at a concentration ranging from about 4 microgram/ml to about 100 microgram/ml,
(v) sodium chloride,
(vi) pH adjusting agent,
(vii) solution having a pH in the range of 3.0 to 4.5,
wherein the solution filled in the infusion container is terminally sterilized by autoclaving, and the solution upon autoclaving and subsequent storage at 40° C./25% relative humidity for a period of at least 6 months contains not more than 0.2% by weight of impurity of Formula I or not more than 0.2% by weight of impurity of Formula II or not more than 0.2% by weight of impurity of Formula III and not more than 1.0% by weight of total impurities, and the solution upon autoclaving and subsequent storage at 25° C./40% relative humidity for a period of at least 18 months contains not more than 0.2% by weight of impurity of Formula I or not more than 0.2% by weight of impurity of Formula II or not more than 0.2% by weight of impurity of Formula III and not more than 1.0% by weight of total impurity.

By the term 'consisting essentially of' means that the aqueous solution of norepinephrine according to the present invention is free of sugar and/or sugar alcohols, and is free of co-solvents like alcohol, propylene glycol or polyethylene glycol.

In a further embodiment the infusion container of the present invention comprises the aqueous solution of norepinephrine or its pharmaceutically acceptable salt, wherein the solution is free of buffers and buffering agents such as tromethamine, lactic acid or its salts, acetic acid or its salts, boric acid or its salt, phosphoric acid or its salt, citric acid or its salt, tartaric acid or its salt, sodium carbonate, sodium hydrogen carbonate, and the like and mixtures thereof.

In yet another embodiment the infusion container of the present invention is filled with an aqueous solution of norepinephrine or pharmaceutically acceptable salt thereof as the sole active ingredient. Norepinephrine or its pharmaceutically acceptable salt is present in therapeutically active amounts. Examples of suitably pharmaceutical acceptable salts of norepinephrine for use in accordance with the present disclosure include hydrochloride, tartrate, bitartrate or other similar salt form. Norepinephrine or its pharmaceutically acceptable salt may be present at a concentration equivalent to about 10 microgram/ml to about 75 microgram/ml of norepinephrine base. In preferred embodiments, the pharmaceutically acceptable salt of norepinephrine is norepinephrine-bitartrate and it is present in the aqueous solution at a concentration equivalent to about 10 microgram/ml to about 75 microgram/ml of norepinephrine base, preferably at a concentration equivalent to about 16 microgram/ml to about 64 microgram/ml of norepinephrine base. In one embodiment, norepinephrine bitartrate is present in an amount equivalent to 16 mcg/ml of norepinephrine base. In another embodiment, norepinephrine bitartrate is present in in an amount equivalent to 32 microgram/ml of norepinephrine base. In yet another embodiment, norepinephrine bitartrate is present in an amount equivalent to 64 microgram/ml of norepinephrine base.

According to the present invention, the aqueous solution of norepinephrine contains at least one sulfite antioxidant such as sodium metabisulfite, optionally one or more other antioxidants, and at least one ion chelator such as ethylenediaminetetraacetic acid or its salt. Combination of these components like antioxidants and ion chelator surprisingly provides enhanced stability to norepinephrine solution such that the dilute, ready-to-infuse aqueous solution of norepinephrine becomes autoclavable and there occurs no substantial increase in the level of impurities upon autoclaving. The content of impurities in the solution remain at lower levels upon autoclaving and long term storage of the dosage form at room temperature (25° C./40% relative humidity) and at accelerated stability condition of 40° C./25% relative humidity compared to the solution that is devoid of sodium metabisulfite or ethylenediaminetetraacetic acid or both. Aqueous solutions which do not contain either a sulfite antioxidant or a chelating agent, or both, instability and the content of impurity of Formula I, Formula II or Formula III or total impurities increase substantially upon autoclaving. This substantial rise in the content of known impurities pose potential threat of toxic or adverse reactions, particularly because the aqueous solution is intended to be administered parenterally through intravenous route and these impurities have been reported to be toxic and having allied unwanted side effects.

The term 'ion chelator' as used herein is also a stabilizer and can be interchangeably used with the term 'chelating agent' or 'metal ion chelator' which may also function as an antioxidant in the composition.

In another embodiment of the present invention may include other antioxidants like butylated hydroxyl anisole, ascorbic acid, sodium ascorbate, propyl gallate, vitamin E or alpha-tocopherol. In some other embodiments antioxidants include butylated hydroxyl anisole and sulfite antioxidants like sodium sulfite, sodium bisulfite, potassium metabisulfite and/or sodium metabisulfite.

In yet another embodiment of the present invention the antioxidant used in the aqueous solution of the present invention is a sulfite antioxidant selected from sodium sulfite, sodium bisulfite, potassium metabisulfite and/or sodium metabisulfite or mixture thereof.

Sodium metabisulfite is present in the aqueous solution according to the present invention in an amount ranging from about 3.0 microgram/ml to about 15 microgram/ml, preferably at a concentration ranging from about 3.2 microgram/ml to about 12.8 microgram/ml, such as for example 3.2, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6 or 12.8 microgram/ml. In one specific embodiment, sodium metabisulfite is present in the aqueous solution at a concentration of 3.2 microgram/ml. In another specific embodiment, sodium metabisulfite is present in the aqueous solution at a concentration of 6.4 microgram/ml. In another specific embodiment, sodium metabisulfite is present in the aqueous solution at a concentration of 12.8 microgram/ml. In one embodiment, the present invention also incorporates the use of other sulfites such as sodium sulfite, sodium bisulfate, and the like.

Ethylenediaminetetraacetic acid or its salts that may be used according to the present invention is selected from but not limited to, ethylenediaminetetraacetic acid, edetic acid, disodium edetate, disodium EDTA, disodium edetate dihydrate, di-potassium edetate, edetate trisodium, edetate calcium disodium, pentasodium pentetate, dipotassium EDTA and the like. Ethylenediaminetetraacetic acid or its salts may be present in the aqueous solution of norepinephrine at a concentration ranging from about 4 microgram/ml to 100 microgram/ml, preferably at a concentration ranging from about 10 microgram/ml to about 75 microgram/ml; more preferably at a concentration ranging from about 16 microgram/ml to about 64 microgram/ml, such as for example, 16, 20, 24, 28, 32, 36, 40, 44, 48, 52, 56, 60 or 64 microgram/ml. Preferably, ethylenediaminetetraacetic acid or its salts is disodium edetate and it is present in the aqueous solution at a concentration ranging from about 4 microgram/ml to 100 microgram/ml, preferably at a concentration ranging from about 16 microgram/ml to about 64 microgram/ml. In one specific embodiment, disodium edetate is present in the aqueous solution at a concentration of 16.0 microgram/ml. In another specific embodiment, disodium edetate is present in the aqueous solution at a concentration of 32.0 microgram/ml. In another specific embodiment, disodium edetate is present in the aqueous solution at a concentration of 64.0 microgram/ml.

The aqueous solution of norepinephrine or its pharmaceutically acceptable salt according to the present invention may further comprise at least one osmogen.

The term 'osmogen' as used herein can be interchangeably used with the term 'tonicity adjusting agent' or 'osmotic agent'.

In yet another embodiment, the non-limiting examples of osmogen used in the aqueous solution of the present invention is selected from sodium chloride, calcium chloride, magnesium chloride, potassium chloride, other inorganic salts, urea, glycerin, glycerol, sucrose, maltose, glycerine, glycerol, xylitol, fructose, mannose, maltitol, inositol or trehalose or mixture thereof.

In another embodiment, the non-limiting examples of osmogen used in the aqueous solution of the present invention is selected from sodium chloride, calcium chloride, magnesium chloride, potassium chloride, other inorganic salts, or urea or mixture thereof.

The aqueous solution of norepinephrine or its pharmaceutically acceptable salt according to the present invention may further comprise at least one pH adjusting agent.

The pH of the solution may be adjusted in the desired range by use of a pH adjusting agents known in the pharmaceutical art or it may be auto-adjusted in the desired range by the ingredients present in the solution of the present invention. The pH adjusting agent that may be used include, but are not limited to sodium hydroxide, hydrochloric acid, sulfuric acid, potassium hydroxide and the like and mixtures thereof.

The aqueous solution of norepinephrine or its pharmaceutically acceptable salt according to the present invention has a pH in the range of about 3.0 to 4.5 preferably from about 3.5 to 4.0, such as for example 3.55, 3.60, 3.65, 3.70, 3.75, 3.80, 3.85, 3.90, 3.95 or 4.0.

In an embodiment, the aqueous solution of norepinephrine according to the present invention has a dissolved oxygen level of less than 4 ppm, preferably less than 2 ppm, more preferably less than 1 ppm. This is achieved by purging the aqueous solution with an inert gas such as nitrogen or argon or helium.

The aqueous solution of norepinephrine or its pharmaceutically acceptable salt may be present in the infusion container in volume ranging from about 50 ml to 1000 ml or 50 ml to 500 ml, preferably from about 100 ml to 500 ml, more preferably from about 100 ml to 250 ml such as for example 100 ml, 110 ml, 120 ml, 125 ml, 130 ml, 140 ml, 150 ml, 160 ml, 170 ml, 175 ml, 180 ml, 190 ml, 200 ml, 210 ml, 220 ml, 225 ml, 230 ml, 240 ml or 250 ml. According to one preferred embodiment, the volume of aqueous solution of norepinephrine filled in the container is 250 ml. In another embodiment, the volume of aqueous solution of norepinephrine filled in the container is 500 ml. The volume capacity of each unit of infusion container may range from about 100 ml to about 500 ml.

According to one embodiment, the infusion container comprises 250 ml of aqueous solution having norepinephrine bitartrate equivalent to 4 mg of norepinephrine base. In another embodiment, the flexible infusion container comprises 250 ml of aqueous solution having norepinephrine bitartrate equivalent to 8 mg of norepinephrine base. In yet another embodiment, the flexible infusion container comprises 250 ml of aqueous solution having norepinephrine bitartrate equivalent to 16 mg of norepinephrine base and the aqueous solution is free of sugar and/or sugar alcohol.

The infusion container filled with an aqueous solution of norepinephrine or its pharmaceutically acceptable salt according to the present invention is also free of solvents and co-solvents like ethanol, glycols such as propylene glycol, polyethylene glycol etc.

According to the present invention, the infusion container filled with an aqueous solution of norepinephrine or its pharmaceutically acceptable salt is free of sugar and/or sugar alcohol like dextrose, lactose, mannitol, sorbitol, and the like. It was surprisingly found by the present inventors that dextrose, mannitol or sorbitol which are commonly used inert excipients, when added to the aqueous solution of norepinephrine and the solution was subjected to autoclaving, there occurred generation of unacceptably high levels of total and known impurities. Particularly, the content of impurity of Formula III increased beyond 0.2% by weight and the content of total impurities increased beyond 1.0% by weight of norepinephrine just after autoclaving of the aqueous solution of norepinephrine. Presence of such high content of impurities is unacceptable as it may cause potential toxic or adverse effects.

The infusion container used in the present invention is generally made up of a flexible material such as plastic or other polymeric material. The infusion container is preferably a flexible infusion container selected from but not limited to an infusion bag, flexible pouch, soft bag, plastic infusion bottle or pre-filled syringe.

The infusion container in some embodiments is packaged in a secondary packaging. The secondary packaging may comprise a suitable pouch, such as an aluminium overwrap pouch covering the primary flexible infusion container. The secondary packaging may further comprise an oxygen scavenger. In yet another embodiment, the space between the flexible infusion container and secondary packaging is occupied with an inert gas. The inert gas may also be used to flush out or replace the air from the space between the flexible infusion container and the light protective secondary packaging.

In yet another embodiment, either of the container or the secondary packaging is designed to protect the solution of norepinephrine from light. They may be made up of a suitable light protective material such as but not limited to aluminum.

Further, the container is designed for ready-to-infuse or ready-to-inject the aqueous solution of norepinephrine to the patient. The container can be made up of a suitable material such as plastic or any other polymeric material. The container may include one or more layers of such materials. Suitably, such materials may include but are not limited to, polyolefin polymers, polyethylene, polypropylene; cyclo olefin polymers, cyclo olefin copolymers, polypropylene based polyolefin polymers; polycarbonates; modified polyolefin-polyethylene polymers or styrene-polyolefin based polymers and block co-polymers thereof. Suitably, the container does not have material that contains borate or boron. Preferably, according to one embodiment, the container has non-glass components. Suitably, the material of construction is such that these containers are transparent which makes it possible to carry out visual inspection of the drug solution prior to and during administration of the drug solution. Any change in colour or any particulate matter can be detected easily by visual inspection, which ensures safety.

In one embodiment, the flexible infusion container includes a thermally resealable portion that is fusible in response to thermal energy, and a container body having a sealed empty chamber in fluid communication with the resealable portion for receiving therein the aqueous solution of the present invention. The method of filling the container includes penetrating the resealable portion with an injection member and introducing the aqueous solution of the present invention into the chamber, withdrawing the injection member while engaging the base of the body to substantially prevent axial movement of the body, and applying thermal energy to the resealable portion to thermally fuse the penetrated region thereof. Such systems are elaborated in U.S. Pat. No. 7,992,597, and a similar system also disclosed in U.S. Pat. No. 7,490,639 which are incorporated herein by reference.

In one embodiment, the infusion container filled with an aqueous solution of norepinephrine or its pharmaceutically acceptable salt has a single outlet for withdrawal of the aqueous solution from the container while being administered intravenously. The container has a single outlet. This design avoids any manipulation, such as volume adjustment (addition or removal of aqueous solution) prior to intravenous infusion.

The infusion container of the present invention filled with an aqueous solution of norepinephrine or its pharmaceutically acceptable salt contains low concentration of norepinephrine. The aqueous drug solution can be directly administered parenterally from the infusion container. It was found by the present inventors that higher the concentration of norepinephrine, it is more stable as compared to the low concentration of norepinephrine. However, the concentrated solutions of norepinephrine needs to be diluted before use to achieve the desired concentration and hence the concentrated solutions though stable, cannot be used as ready to infuse solutions as the term "ready-to-infuse' or 'directly administering' or 'direct intravenous infusion' or 'direct delivery' or 'ready to administer' refers to direct intravenous infusion of the aqueous drug solution to the patient without involving any intermediate steps of manipulation, dilution, reconstitution, dispensing, sterilization, transfer, handling or compounding before intravenous parenteral administration of the drug solution.

According to one aspect of process of the present invention, the aqueous solution of norepinephrine or its pharmaceutically acceptable salt filled in an infusion container is terminally sterilized by autoclaving. The terminal sterilization is achieved by autoclaving or moist heat sterilization technique wherein, the filled and the sealed container is terminally sterilized in an autoclave. The autoclaving may be carried out at temperature varying from about 110° C. to 125° C. for a period of time varying from about 5 minutes to 60 minutes and at pressure of about 2.0 to 3.5 bar. Preferably, autoclaving is carried out at a temperature of 121° C. and pressure of 3.5 bar for a period of 15 minutes.

In another embodiment, the present invention also provides a method for stabilizing an aqueous solution of norepinephrine in a ready to infuse infusion bag using a combination of at least one sulfite antioxidant and ethylenediaminetetraacetic acid or its salts, wherein the aqueous solution can be characteristically terminally sterilized by autoclaving.

In another embodiment the present invention provides a method for stabilizing an aqueous solution of norepinephrine by terminal sterilization using autoclaving, wherein the stability of the solution is characterized by the impurity content of not more than 0.2% by weight of impurity of Formula I or not more than 0.2% by weight of impurity of Formula II or not more than 0.2% by weight of impurity of Formula III and not more than 1.0% by weight of total impurities when stored at 40° C./25% relative humidity for a period of at least 6 months; and the impurity content of not more than 0.2% by weight of impurity of Formula I or not more than 0.2% by weight of impurity of Formula II or not more than 0.2% by weight of impurity of Formula III and not more than 1.0% by weight of total impurities when stored at room temperature for a period of 18 months or longer.

In yet another embodiment the present invention provides a method for using a combination of antioxidants and chelating agent for stabilizing an aqueous solution of norepinephrine in a ready to infuse infusion bag, wherein the said infusion bag can be terminally sterilized by autoclaving and which upon storage at 40° C./25% relative humidity for a period of at least 6 months or at room temperature for a period of at least 18 months, remains physically and chemically stable such that the content of known impurity of Formula I, Formula II or Formula III remains not more than 0.2% by weight of norepinephrine, and the content of total impurities remains not more than 1.0% by weight of norepinephrine and there occurs not more than 5% drop in the content of norepinephrine.

In a further embodiment the present invention provides a method for treatment of hypotensive states comprising: administering an infusion of a ready to infuse stable aqueous infusion solution of Norepinephrine or its pharmaceutically acceptable salt at a concentration equivalent to about 10 µg/ml to about 75 µg/ml of norepinephrine base, wherein the solution is terminally sterilized by autoclaving in a infusion container.

In yet another embodiment the present invention provides a dosage form for intravenous administration for treatment of hypotensive conditions, comprising an infusion bag comprising storage stable aqueous infusion solution of Norepinephrine or its pharmaceutically acceptable salt at a concentration equivalent to about 10 µg/ml to about 75 µg/ml of norepinephrine base, preferably at a concentration equivalent to about 16 µg/ml to about 64 µg/ml of norepinephrine base.

In another embodiment the present invention provides a method for administration of a peripheral vasoconstrictor or an inotropic stimulator of the heart and dilator of coronary artery in a single-dose of ready to use intravenous infusion into a large vein of the patient requiring a treatment for hypotensive states, wherein the single dose of the ready to use infusion comprises norepinephrine in a concentration range of about 10 to 75 µg/ml of norepinephrine base.

In yet another embodiment the present invention provides a method for restoration of blood pressure in acute hypertension, comprising administering a ready to use storage stable infusion of norepinephrine in an infusion bag through an intravenous drip chamber or suitable metering device at an initial low dose of 8-12 micrograms of base per minute for observing the response followed by adjusting the rate of flow to establish and maintain a low normal blood pressure sufficient to maintain the circulation to vital organs. In one embodiment, the present invention also provides method for restoration of blood pressure in previously hypertensive patients using an average dose of 2-4 microgram per minute to maintain the blood pressure below 40 mm Hg below the preexisting systolic pressure.

An infusion container filled with an aqueous solution of norepinephrine or its pharmaceutically acceptable salt according to the present invention is suitable for controlling blood pressure in acute hypotensive states such as pheochromocytomectomy, sympathectomy, poliomyelitis, spinal anesthesia, myocardial infarction, septicemia, blood transfusion, and drug reactions.

The present invention thus provides a method of restoration of blood pressure in acute hypotensive states selected from the group consisting of pheochromocytomectomy, sympathectomy, poliomyelitis, spinal anesthesia, myocardial infarction, septicemia, blood transfusion, or drug reactions, the method comprising intravenously administering aqueous solution of norepinephrine through the infusion container according to the present invention.

In some embodiments, the infusion container filled with an aqueous solution of norepinephrine or its pharmaceutically acceptable salt according to the present invention is used as an adjunctive treatment in the treatment of cardiac arrest and profound hypotension.

Hereinafter, the invention will be more specifically described by way of Examples. The examples are not intended to limit the scope of the invention and are merely used as illustrations. It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in any appropriately detailed structure.

EXAMPLES

Example 1 to 3

The examples 1-3 illustrate infusion containers filled with an aqueous solution of norepinephrine bitartrate, according to the present invention:

TABLE 1

Composition of aqueous solution:

| | | Amount (microgram/mL) | | |
|---|---|---|---|---|
| Sr. No. | Ingredients | Example 1 | Example 2 | Example 3 |
| 1 | Norepinephrine bitartrate USP equivalent to Norepinephrine base | 16.0 | 32.0 | 64.0 |
| 2 | Sodium metabisulfite | 3.2 | 6.4 | 12.8 |
| 3 | Disodium Edetate (EDTA) | 16.0 | 32.0 | 64.0 |
| 4 | Butylated hydroxyanisole | 0.1 | 0.2 | 0.4 |
| 5 | Sodium chloride | | 9000.0 | |

TABLE 1-continued

| | | Composition of aqueous solution: | | |
|---|---|---|---|---|
| | | | Amount (microgram/mL) | |
| Sr. No. | Ingredients | Example 1 | Example 2 | Example 3 |
| 6 | Water for Injection | q.s. | | |
| 7 | Sodium hydroxide/ hydrochloric acid | q.s. to adjust pH | | | q.s.—quantity sufficient

Manufacturing process: Specified quantity of water for injection was taken in a container and was purged with nitrogen to reduce the dissolved oxygen level below 1 ppm (parts per million). Specified quantity of ethylenediaminetetraacetic acid or its salt was added to this water for injection and dissolved under stirring. To this, specified quantity of sodium chloride was added and dissolved under stirring. Subsequently, specified quantity of stock solution of butylated hydroxyanisole was also added and dissolved under stirring. To the above solution, specified quantity of sodium metabisulfite was added and dissolved under stirring. This was followed by addition of specified quantity of norepinephrine bitartrate, which was dissolved under stirring. The pH of the solution was adjusted to about 3.75 using hydrochloric acid/sodium hydroxide. The final volume was made to 100 ml with water for injection and mixed well under stirring. The solution was aseptically filtered through 0.2 μm filter and filled into a flexible infusion bag (container). Nitrogen was continuously purged during the course of the process to maintain the dissolved oxygen level below 1 ppm. The filled infusion bags of example 1, 2 and 3 were terminally sterilized by autoclaving at a temperature of about 121° C. for 15 minutes. The autoclaved bags were wrapped using an aluminium pouch with nitrogen flushing and an oxygen scavenger was kept in between the bag and the overwrap pouch.

The % assay of norepinephrine, % total impurity, % known impurities having Formula I, Formula II and Formula III and % of highest unknown impurity was quantified by high performance liquid chromatography (HPLC) method using a suitable column like C18 or any other column as per impurity to be detected, with mobile phase flow rate, wavelength, run time, injection volume, and sample cooler/ column temperature specific to norepinephrine or impurity. The samples were analysed before and after autoclaving and upon storage at different time points. The results of effect of autoclaving on the impurity levels I, II and III and total impurities are presented in Table 2.

TABLE 2

Results of chemical analysis: Effect of autoclaving on impurity levels I, II and III

| | | | Impurity Levels | | | | |
|---|---|---|---|---|---|---|---|
| Example | Stability condition | % Assay of Norepinephrine (90-115%) | Impurity Formula I (NMT 0.2%) | Impurity Formula II (NMT 0.2%) | Impurity Formula III (NMT 0.2%) | Unknown Impurity (NMT 0.2%) | Total Impurities (NMT 1%) |
| Ex. 1 (16 μg/ml) | Autoclaved (Initial) | 99.29 | 0.02 | 0.03 | 0.07 | 0.02 | 0.27 |
| | 40° C./25% RH  3 M | 100.32 | 0.03 | 0.02 | 0.08 | 0.02 | 0.31 |
| | 25% RH  6 M | 98.11 | 0.04 | 0.02 | 0.07 | 0.05 | 0.39 |
| | 25° C./40% RH  18 M | 99.16 | 0.05 | 0.03 | 0.05 | ND | 0.20 |
| Ex. 2 (32 μg/ml) | Autoclaved (Initial) | 101.1 | 0.02 | 0.03 | 0.07 | 0.05 | 0.37 |
| | 40° C./25% RH  3 M | 100.88 | 0.02 | 0.02 | 0.07 | 0.05 | 0.40 |
| | 25° C./  3 M | 100.8 | 0.02 | 0.02 | 0.06 | 0.05 | 0.35 |
| | 40% RH  18 M | 100.95 | ND | ND | 0.07 | 0.06 | 0.13 |
| Ex. 3 (64 μg/ml) | Autoclaved (Initial) | 100.51 | 0.01 | 0.02 | 0.04 | 0.05 | 0.35 |
| | 40° C./  3 M | 100.62 | 0.01 | 0.01 | 0.03 | 0.05 | 0.33 |
| | 25% RH  6 M | 100.94 | 0.01 | 0.00 | 0.02 | 0.05 | 0.36 |
| | 25° C./  3 M | 100.8 | 0.01 | 0.01 | 0.05 | 0.05 | 0.31 |
| | 40% RH  6 M | 101.96 | 0.01 | 0.01 | 0.02 | 0.05 | 0.29 |
| | 12 M | 99.11 | ND | ND | ND | ND | 0.08 |
| | 18 M | 99.34 | ND | ND | ND | 0.04 | 0.11 |

RH—Relative Humidity

It was found that upon autoclaving, the solutions remained clear and colorless, without any signs of precipitation or crystallization or color change upon storage. It was further observed that the solution had less than 1.0% by weight of total impurities, less than 0.2% by weight of highest unknown impurity and less than 0.2% by weight of Impurity of Formula I, Formula II or Formula III, after autoclaving. The impurity levels were maintained and were found to be very low even after storage of the solution at 40° C./25% RH for 3 and 6 months and at 25° C./40% RH for 3, 6, 12 and 18 months respectively. Similarly various other batches were also prepared and loaded for stability and found to be stable, the above Table 2 represents the stability data of one of the batch.

Example 4 to 6

Example 4: The examples 4 illustrate infusion containers filled with an aqueous solution of various compositions of norepinephrine bitartrate equivalent to about 16 μg/ml of norepinephrine base, according to the present invention:

TABLE A

Composition of aqueous solution:

| Ingredients | Amount (microgram/mL) | | | | | | | | |
|---|---|---|---|---|---|---|---|---|---|
| | 4a | 4b | 4c | 4d | 4e | 4f | 4g | 4h | 4i |
| Norepinephrine bitartrate USP equivalent to Norepinephrine base | | | | | 16.0 | | | | |
| Sodium sulfite | 8.0 | — | — | — | — | — | — | — | — |
| Sodium metabisulfite | — | — | — | 3.2 | 3.2 | 3.2 | 3.2 | 3.2 | 3.2 |
| Sodium bisulfite | — | 18.0 | — | — | — | — | — | — | — |
| Potassium Metabisulfite | — | — | 2.4 | — | — | — | — | — | — |
| Edetic Acid | — | — | — | 0.8 | — | — | — | — | — |
| Edetate Trisodium | — | — | — | — | 14.8 | — | — | — | — |
| Edetate Sodium | — | — | — | — | — | 1.6 | — | — | — |
| Edetate Calcium Disodium | — | — | — | — | — | — | — | 8.6 | — |
| Disodium Edetate (EDTA) | 16.0 | 16.0 | 16.0 | — | — | — | 16.0 | — | — |
| Pentasodium Pentetate | — | — | — | — | — | — | — | — | 20.0 |
| Butylated hydroxyanisole | 0.1 | 0.1 | 0.1 | 0.1 | 0.1 | 0.1 | — | 0.1 | 0.1 |
| Sodium chloride | | | | | 9000.0 | | | | |
| Water for Injection | | | | | q.s. | | | | |
| Sodium hydroxide/ hydrochloric acid | | | | | q.s. to adjust pH | | | | |

Manufacturing process: Specified quantity of water for injection was taken in a container and was purged with nitrogen to reduce the dissolved oxygen level below 1 ppm (parts per million). Specified quantity of specified ion chelator was added to this water for injection and dissolved under stirring. To this, specified quantity of sodium chloride was added and dissolved under stirring. Subsequently, specified quantity of stock solution of butylated hydroxyanisole was also added and dissolved under stirring. To the above solution, specified quantity of sulfite antioxidant was added and dissolved under stirring. This was followed by addition of specified quantity of norepinephrine bitartrate, which was dissolved under stirring. The pH of the solution was adjusted to about 3.75 using hydrochloric acid/sodium hydroxide. The final volume was made to 100 ml with water for injection and mixed well under stirring. The solution was aseptically filtered through 0.2 μm filter and filled into a flexible infusion bag (container). Nitrogen was continuously purged during the course of the process to maintain the dissolved oxygen level below 1 ppm. The filled infusion bags of example 4 were terminally sterilized by autoclaving at a temperature of about 121° C. for 15 minutes. The autoclaved bags were wrapped using an aluminium pouch with nitrogen flushing and an oxygen scavenger was kept in between the bag and the overwrap pouch.

Example 5: The examples 5 illustrate infusion containers filled with an aqueous solution of various compositions of norepinephrine bitartrate equivalent to about 32 μg/ml of norepinephrine base, according to the present invention:

TABLE B1

Composition of aqueous solution:

| Ingredients | Amount (microgram/mL) | | | | | | | | |
|---|---|---|---|---|---|---|---|---|---|
| | 5a | 5b | 5c | 5d | 5e | 5f | 5g | 5h | 5i |
| Norepinephrine bitartrate USP equivalent to Norepinephrine base | | | | | 32.0 | | | | |
| Sodium sulfite | 8.0 | — | — | — | — | — | — | — | — |
| Sodium metabisulfite | — | — | — | 3.2 | 3.2 | 3.2 | 3.2 | 3.2 | 3.2 |
| Sodium bisulfite | — | 18.0 | — | — | — | — | — | — | — |
| Potassium Metabisulfite | — | — | 2.4 | — | — | — | — | — | — |
| Edetic Acid | — | — | — | 0.8 | — | — | — | — | — |
| Edetate Trisodium | — | — | — | — | 14.8 | — | — | — | — |
| Edetate Sodium | — | — | — | — | — | 1.6 | — | — | — |
| Edetate Calcium Disodium | — | — | — | — | — | — | — | 8.6 | — |
| Disodium Edetate (EDTA) | 16.0 | 16.0 | 16.0 | — | — | — | 16.0 | — | — |
| Pentasodium Pentetate | — | — | — | — | — | — | — | — | 20.0 |
| Butylated hydroxyanisole | 0.1 | 0.1 | 0.1 | 0.1 | 0.1 | 0.1 | 0.1 | 0.1 | 0.1 |
| Sodium chloride | | | | | 9000.0 | | | | |
| Water for Injection | | | | | q.s. | | | | |
| Sodium hydroxide/ hydrochloric acid | | | | | q.s. to adjust pH | | | | |

Manufacturing process: Same as Example 4.

Example 6: The examples 6 illustrate infusion containers filled with an aqueous solution of various compositions of norepinephrine bitartrate equivalent to about 64 µg/ml of norepinephrine base, according to the present invention:

TABLE B2

Composition of aqueous solution:

| Ingredients | Amount (microgram/mL) | | | | | | | | |
|---|---|---|---|---|---|---|---|---|---|
| | 6a | 6b | 6c | 6d | 6e | 6f | 6g | 6h | 6i |
| Norepinephrine bitartrate USP equivalent to Norepinephrine base | | | | | 64.0 | | | | |
| Sodium sulfite | 8.0 | — | — | — | — | — | — | — | — |
| Sodium metabisulfite | — | — | — | 3.2 | 3.2 | 3.2 | 3.2 | 3.2 | 3.2 |
| Sodium bisulfite | — | 18.0 | — | — | — | — | — | — | — |
| Potassium Metabisulfite | — | — | 2.4 | — | — | — | — | — | — |
| Edetic Acid | — | — | — | 0.8 | — | — | — | — | — |
| Edetate Trisodium | — | — | — | — | 14.8 | — | — | — | — |
| Edetate Sodium | — | — | — | — | — | 1.6 | — | — | — |
| Edetate Calcium Disodium | — | — | — | — | — | — | — | 8.6 | — |
| Disodium Edetate (EDTA) | 16.0 | 16.0 | 16.0 | — | — | — | 16.0 | — | — |
| Pentasodium Pentetate | — | — | — | — | — | — | — | — | 20.0 |
| Butylated hydroxyanisole | 0.1 | 0.1 | 0.1 | 0.1 | 0.1 | 0.1 | 0.1 | 0.1 | 0.1 |
| Sodium chloride | | | | | 9000.0 | | | | |
| Water for Injection | | | | | q.s. | | | | |
| Sodium hydroxide/ hydrochloric acid | | | | | q.s. to adjust pH | | | | |

Manufacturing process: Same as Example 4.

Comparative Examples 1 to 12

TABLE 3

Composition of aqueous solution

| Ingredients | Amount (microgram/mL) Comparative Examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Norepinephrine | | | | | | 16 | | | | 4 | 8 | 16 |
| Sodium metabisulfite | — | 3.2 | 3.2 | — | 3.2 | | | 3.2 | | 3.2 | 3.2 | 0.8 |
| Disodium Edetate (EDTA) | 16 | — | — | 16 | — | | | 16 | | 16 | 16 | 4 |
| Butylated hydroxyanisole | — | 0.1 | — | 0.1 | — | | | 0.1 | | 0.1 | 0.1 | 0.025 |
| Dextrose Monohydrate | — | — | — | — | 50000 | | | — | — | — | | |
| Mannitol | — | — | — | — | — | — | 50000 | — | — | — | | |
| Sorbitol | — | — | — | — | — | — | — | — | 50000 | — | | |
| Lactose Monohydrate | — | — | — | — | — | — | — | — | — | 100000 | — | |
| Sodium Chloride | | 9000 | | | — | — | | — | — | | 9000 | |
| Water for Injection | | | | | | q.s | | | | | | |
| Sodium hydroxide/ hydrochloric acid | | | | | q.s. to adjust pH to about 3.75 | | | | | | | | q.s.—quantity sufficient

The comparative examples 1 to 12 having the compositions as described in table 3 were prepared by manufacturing process similar to one described in examples 1 to 3. Specified quantity of ingredients were mixed and dissolved in water for injection to make clear solution. The solution was aseptically filtered through 0.2 µm filter and filled into flexible infusion bag (container). The filled infusion bags were terminally sterilized by autoclaving at a temperature of about 121° C. for 15 minutes. The autoclaved bags were wrapped with an aluminium pouch with nitrogen flushing and an oxygen scavenger was kept in between the bag and the overwrap pouch and the bags were kept for storage stability testing.

The solutions of comparative examples 1 to 12 were subjected to chemical analysis and the percentage of known impurities of Formula I, Formula II and Formula III, highest unknown impurity and total impurities were quantified by HPLC method. The results of effect of autoclaving on the impurity levels I, II and III are presented below in Table 4.

TABLE 4

Results of chemical analysis: Effect of autoclaving on impurity levels I, II and III.

Impurity Levels (% by weight of Norepinephrine)

| Comparative Example | Condition (Initial) | Impurity of Formula I | Impurity of Formula II | Impurity of Formula III | Total Impurities | Conclusion |
|---|---|---|---|---|---|---|
| 1. | Autoclaved | 0.12 | 0.15 | 0.26 | 0.78 | When only EDTA was present, and sodium metabisulfite was absent, substantial increase in the level of the impurity of Formula I, impurity of Formula II and impurity of Formula III was observed. |
| 2. | Autoclaved | 0.02 | 0.03 | 0.34 | 1.90 | When EDTA was absent, then inspite of presence of sodium metabisulfite and butylated hydroxyanisole, substantial increase in the level of impurity of Formula III was observed. |
| 3. | Autoclaved | 0.03 | 0.05 | 0.22 | 0.85 | When only sodium metabisulfite was present, substantial increase in the level of impurity of Formula III was observed |
| 4. | Autoclaved | 0.12 | 0.14 | 0.25 | 0.70 | When EDTA and butylated hydroxyanisole were present, but sodium metabisulfite was absent, substantial increase in the level of impurity of Formula I, impurity of Formula II and impurity of Formula III was observed. |
| 5. | Autoclaved | 0.17 | 0.21 | 0.36 | 1.51 | When dextrose was used as tonicity agent instead of sodium chloride and sodium metabisulfite alone was used as stabilizing agent, increase in the level of the impurity of Formula I, impurity of Formula II and impurity of Formula III was observed. |
| 6. | Autoclaved | 0.13 | 0.12 | 0.45 | 2.14 | When dextrose was used as tonicity agent instead of sodium chloride, then inspite of presence of a EDTA and sodium metabisulfite, an increase in the level of impurity of Formula I, impurity of Formula II and impurity of Formula III was observed. |
| 7. | Autoclaved | 0.07 | 0.27 | 0.24 | 0.86 | When mannitol was used as tonicity agent instead of sodium chloride, then inspite of presence of EDTA and sodium metabisulfite, an increase in the level of impurity of Formula II and impurity of Formula III was observed. |
| 8. | Autoclaved | 0.07 | 0.28 | 0.26 | 1.11 | When sorbitol was used as tonicity agent instead of sodium chloride, then inspite of presence of EDTA and sodium metabisulfite, an increase in the level of impurity of Formula II and impurity of Formula III was observed. |

TABLE 4-continued

Results of chemical analysis: Effect of autoclaving on impurity levels I, II and III.

| Comparative Example | Condition (Initial) | Impurity of Formula I | Impurity of Formula II | Impurity of Formula III | Total Impurities | Conclusion |
|---|---|---|---|---|---|---|
| 9. | Autoclaved | 0.15 | 0.34 | 0.13 | 3.01 | When lactose was used as tonicity agent instead of sodium chloride, then inspite of presence of a EDTA and sodium metabisulfite, an increase in the level of the impurity of Formula I, impurity of Formula II and impurity of Formula III was observed. |
| 10. | Autoclaved | 0.05 | 0.05 | 0.14 | 0.39 | When the concentration of norepinephrine was low that is 4 mcg/ml, increase in the level of the impurity of Formula III was observed. |
| 11. | Autoclaved | 0.05 | 0.05 | 0.11 | 0.40 | When the concentration of norepinephrine was low that is 8 mcg/ml, increase in the level of the impurity of Formula III was observed. |
| 12. | Autoclaved | 0.05 | 0.07 | 0.13 | 0.43 | When the concentration of all the excipients viz. EDTA, sodium metabisulfite, and butylated hydroxyanisole was reduced 4 times keeping the concentration of norepinephrine as 16 mcg/ml, increase in the level of the impurity of Formula III was observed. |

From the above data, it was observed that solutions as per comparative examples could not withstand autoclaving and there occurred substantial increase in the levels of impurity of Formula I, Formula II or Formula III, or highest unknown impurity and/or total impurity levels. This indicates that unique combination of at least one antioxidants like sodium metabisulphite, and a metal ion chelator like ethylenediaminetetetraacetic acid salt at specified concentration is essential to provide a solution of norepinephrine which is stable, autoclavable and robust. From the above data it was also observed that any one of the impurity of Formula I, Formula II or Formula III can increase when the solution is not prepared according to the present invention (see comparative example 1 to 12).

From the above data of comparative example 5, 6, 7, 8 and 9 it was observed that when the parenteral dosage form of norepinephrine was manufactured using dextrose, mannitol, sorbitol and lactose and the solution was subjected to autoclaving, drastic increase in the level of known impurities, viz impurity of Formula I, Formula II or Formula III was observed.

Examples 13-20

TABLE 5

Composition of aqueous solution using various combinations of components:

| Ingredients | Amount (microgram/mL) Examples | | | | | | | |
|---|---|---|---|---|---|---|---|---|
| | 13 | 14 | 15 | 16 | 17 | 18 | 19 | 20 |
| Norepinephrine | 16 | | | | | | | |
| Sodium metabisulfite | — | — | — | 3.2 | 3.2 | 3.2 | — | 3.2 |
| Butylated hydroxyanisole | — | 0.1 | — | — | 0.1 | — | 0.1 | 0.1 |
| Disodium Edetate (EDTA) | — | — | 16 | — | — | 16 | 16 | 16 |
| Sodium Chloride | 9000 | | | | | | | |
| Water for Injection | q.s | | | | | | | |
| Sodium hydroxide/ hydrochloric acid | q.s. to adjust pH to about 3.75 | | | | | | | |

The examples 13 to 20 having the compositions as described in table 5 were prepared by manufacturing process similar to one described in examples 1 to 3. Specified quantity of ingredients were mixed and dissolved in water for injection to make clear solution. The solution was aseptically filtered through 0.2 μm filter and filled into flexible infusion bag (container). The filled infusion bags were terminally sterilized by autoclaving at a temperature of about 121° C. for 15 minutes. The autoclaved bags were wrapped with an aluminium pouch with nitrogen flushing and an oxygen scavenger was kept in between the bag and the overwrap pouch and the bags were kept for storage stability testing.

The solutions of examples 13 to 20 were subjected to chemical analysis and the percentage of known impurities of Formula I, Formula II and Formula III, highest unknown impurity and total impurities were quantified by HPLC method. The results of effect of autoclaving on the impurity levels I, II and III are presented below in Table 6.

Example 19 also despite having combination of antioxidant and ion chelator (BHA+EDTA) showed an increase in total impurity and Impurity of Formula III in initial and Formula I in storage sample after 2 weeks of stability study.

Example 18 with combination of antioxidant and ion chelator (SMB+EDTA) and Example 20 with combination of antioxidants and ion chelator (SMB+BHA+EDTA) showed significant stability in 3 month and 6

TABLE 6

Results of effect of different antioxidants and chelating agent and their combinations on stability of Norepinephrine dosage form and resulting impurity levels:

| | | | | Impurity Levels (% by weight of Norepinephrine) | | | |
|---|---|---|---|---|---|---|---|
| | Stage | | | Impurity of | Impurity of | Impurity of | Total |
| Example | Condition (Autoclaved) | Month | % Assay (90-115%) | Formula I (NMT 0.2%) | Formula II (NMT 0.2%) | Formula III (NMT 0.2%) | Impurity (NMT 1%) |
| Ex. 13 (NE) | Initial | 0 | 98.6 | 0.08 | 0.08 | 0.03 | 0.47 |
| | 40° C./25% RH | 0.5 | 99.35 | 0.24 | 0.12 | 0.02 | 0.77 |
| Ex. 14 (NE + BHA) | Initial | 0 | 102.09 | 0.07 | 0.08 | 0.03 | 0.45 |
| | 40° C./25% RH | 0.5 | 103.58 | 0.21 | 0.11 | 0.02 | 0.84 |
| Ex. 15 (NE + EDTA) | Initial | 0 | 98.61 | 0.12 | 0.15 | 0.26 | 0.78 |
| | 40° C./25% RH | 0.5 | 100.76 | 0.37 | 0.18 | 0.14 | 1.06 |
| Ex. 16 (NE + SMB) | Initial (UA) | 0 | 100.52 | ND | ND | ND | 0.29 |
| | Initial | 0 | 99.4 | 0.03 | 0.05 | 0.22 | 0.85 |
| | 40° C./25% RH | 0.5 | — | — | — | — | — |
| Ex. 17 (NE + SMB + BHA) | Initial | 0 | 100.12 | 0.02 | 0.03 | 0.34 | 1.90 |
| | 40° C./25% RH | 0.5 | — | — | — | — | — |
| Ex. 18 (NE + SMB + EDTA) | Initial | 0 | 99.83 | 0.03 | 0.03 | 0.06 | 0.25 |
| | 25° C./40% RH | 1 | 99.81 | 0.02 | 0.03 | 0.03 | 0.23 |
| | 40° C./25% RH | 3 | 99.18 | 0.03 | 0.02 | 0.07 | 0.31 |
| Ex. 19 (NE + BHA + EDTA) | Initial | 0 | 102 | 0.12 | 0.14 | 0.25 | 0.70 |
| | 40° C./25% RH | 0.5 | 102.70 | 0.34 | 0.18 | 0.13 | 0.94 |
| Ex. 20 (NE + SMB + BHA + EDTA) | Initial | 0 | 98.5 | 0.04 | 0.06 | 0.09 | 0.36 |
| | 40° C./25% RH | 0.5 | 101.18 | 0.05 | 0.07 | 0.04 | 0.34 |
| | | 6 | 101.72 | 0.08 | 0.04 | 0.10 | 0.59 |

ND: Not detected, UA: Un-autoclave, NE: Norepinephrine, BHA: Butylated hydroxyanisole, EDTA: Disodium Edetate, SMB: Sodium metabisulfite, RH: Relative Humidity, NMT: Not more than.

From the above data, it was observed that some of the solutions as per examples 13-20 could not withstand autoclaving and there occurred substantial increase in the levels of impurity of Formula I, Formula II or Formula III, total impurity levels with different combination of components and antioxidants.

Examples 13 without any anti-oxidant and Example 14-15 with either antioxidant or ion chelator respectively showed increase in total impurity within 2 weeks of stability analysis, and the level of Impurity of Formula I significantly increased in all three examples.

Example 16 with single antioxidant was analysed without autoclaving as well as with autoclaving and there was a significant increase in Impurity of Formula III and total impurity in the initial stage hence sample not loaded for stability.

Also, Example 17 despite having combination of antioxidants and ion chelator (BHA+EDTA) showed a significant increase in total impurity and Impurity of Formula III in the initial samples hence sample not loaded for stability.

months samples under stress. This indicates that unique combination of one or more antioxidants with chelating agent like ethylenediaminetetraacetic acid or disodium edetate (EDTA) at specified concentration is essential to provide a solution of norepinephrine which is stable, autoclavable and robust. From the above data, it was also observed that any one of the impurity of Formula I, Formula II or Formula III can increase when the solution is not prepared according to the present invention.

From the above examples and the above embodiments as depicted throughout the present specification it was observed that parenteral dosage form of norepinephrine with above stated combination of components is a stable and robust composition or dosage form which can withstand terminal sterilization by autoclaving and can be used as ready to administer dosage form without any further dilution, reconstitution or handling requirements. Such dosage form can be autoclaved and is stable at room temperature for a period of at least 18 months and upon storage at 40° C./25% relative humidity for a period of at least 6 months.

The invention claimed is:

1. A ready to infuse stable parenteral dosage form consisting essentially of:
   a. norepinephrine or its pharmaceutically acceptable salt at a concentration ranging from 10 to 75 micrograms/ml of norepinephrine base;
   b. at least one sulfite antioxidant;
   c. at least one ion chelator; and
   d. sodium chloride,
wherein the dosage form is an aqueous solution and was terminally sterilized by autoclaving;
wherein the content of total impurities of norepinephrine in the sterilized solution, after storage at 40° C./25% RH for 6 months, is not more than 1% by weight of norepinephrine; and
wherein the dosage form, when stored at room temperature, is stable for a period of at least 18 months.

2. The ready to infuse dosage form of claim 1, wherein the dosage form further comprises at least one osmogen.

3. The ready to infuse dosage form of claim 1, wherein the dosage form is free of sugar and sugar alcohol.

4. The ready to infuse dosage form of claim 2, wherein the osmogen is selected from one or more of sodium chloride, calcium chloride, magnesium chloride, potassium chloride, inorganic salts, urea, glycerin, glycerol, sucrose, xylitol, fructose, maltitol, mannose, inositol, and trehalose.

5. The ready to infuse dosage form of claim 1, wherein the dosage form further comprises at least one pH adjusting agent.

6. The ready to infuse dosage form of claim 1, wherein the sulfite antioxidant is selected from one or more of sodium sulfite, potassium metabisulfite, sodium bisulfite, and sodium metabisulfite.

7. The ready to infuse dosage form of claim 1, wherein the dosage form further comprises an antioxidant selected from one or more of butylated hydroxyl anisole, ascorbic acid, sodium ascorbate, propyl gallate, vitamin E, and alpha-tocopherol.

8. The ready to infuse dosage form of claim 1, wherein the ion chelator is selected from one or more of ethylenediaminetetraacetic acid (EDTA), edetic acid, disodium edetate dihydrate, disodium EDTA, di-potassium edetate, dipotassium EDTA, edetate calcium disodium, edetate trisodium, pentasodium pentetate, diethylenetriamine, and pentaacetic acid.

9. The ready to infuse dosage form of claim 1, wherein norepinephrine or its pharmaceutically acceptable salt is present at a concentration ranging from about 16 to about 64 microgram/ml of norepinephrine base.

10. The ready to infuse dosage form of claim 1, wherein the sulfite antioxidant is present at a concentration ranging from about 3 to about 15 microgram/ml.

11. The ready to infuse dosage form of claim 1, wherein the ion chelator is present at a concentration ranging from about 4 to about 100 microgram/ml.

12. The ready to infuse dosage form of claim 8, wherein the ion chelator is disodium edetate.

13. The ready to infuse dosage form of claim 8, wherein the ion chelator is EDTA or its salt and present at a concentration ranging from about 16 microgram/ml to about 64 microgram/ml.

14. The ready to infuse dosage form of claim 1, wherein the pH of the aqueous solution is in the range of 3.0 to about 4.5.

15. The ready to infuse dosage form of claim 1, wherein the dosage form is filled in an infusion container.

16. The ready to infuse dosage form of claim 15, wherein the dosage form is further packaged in a secondary packaging.

17. The ready to infuse dosage form of claim 16, wherein the secondary packaging comprises an aluminium pouch.

18. The ready to infuse dosage form of claim 16, wherein a space between the infusion container and the secondary packaging is occupied with an oxygen scavenger or an inert gas.

19. The ready to infuse dosage form of claim 15, wherein the infusion container is made up of a material selected from plastic; polyolefin polymers; polyethylene; polypropylene; cyclo olefin polymers; cyclo olefin copolymers; polypropylene based polyolefin polymers; polycarbonates; modified polyolefinpolyethylene polymers; styrene-polyolefin based polymers; and block co-polymers thereof.

20. A method for controlling blood pressure in an acute hypotensive state selected from the group consisting of pheochromocytomectomy, sympathectomy, poliomyelitis, spinal anesthesia, myocardial infarction, septicemia, blood transfusion, and a drug reaction, wherein the method comprises administering a ready to infuse dosage form of claim 1.

21. An infusion container filled with a ready to infuse stable aqueous solution of norepinephrine, the solution consisting essentially of:
   norepinephrine bitartrate at a concentration equivalent to about 10 microgram/ml to about 75 microgram/ml of norepinephrine base,
   sodium metabisulfite at least one sulfite antioxidant at a concentration ranging from about 3 microgram/ml to about 15 microgram/ml,
   disodium edetate at a concentration ranging from about 4 microgram/ml to about 100 microgram/ml,
   butylated hydroxyanisole at a concentration ranging from about 0.1 microgram/ml to about 0.4 microgram/ml, and
   sodium chloride,
wherein (i) the solution filled in the infusion container was terminally sterilized by autoclaving, and (ii) the solution has a pH of 3 to 4.5.

22. The infusion container of claim 21, wherein the solution, when subjected to autoclaving at about 121° C. for 15 minutes and stored at 40° C. and 25% relative humidity for 6 months, contains no more than 0.2% by weight of 3,4-dihydroxybenzaldehyde.

23. The infusion container of claim 21, wherein the solution filled in the infusion container was terminally sterilized by autoclaving at 121° C. for 15 minutes.

24. The ready to infuse dosage form of claim 1, wherein the dosage form, when subjected to autoclaving at about 121° C. for 15 minutes, contains no more than 0.2% by weight of 3,4-dihydroxybenzaldehyde.

25. The ready to infuse dosage form of claim 1, wherein the dosage form was terminally sterilized by autoclaving at 121° C. for 15 minutes.

* * * * *

UNITED STATES PATENT AND TRADEMARK OFFICE
CERTIFICATE OF CORRECTION

PATENT NO. : 11,197,838 B2
APPLICATION NO. : 16/989027
DATED : December 14, 2021
INVENTOR(S) : Kumar et al.

Page 1 of 1

It is certified that error appears in the above-identified patent and that said Letters Patent is hereby corrected as shown below:

In the Claims

Claim 21, Column 28, Line 35, delete "at least one sulfite antioxidant"

Signed and Sealed this
Fourth Day of October, 2022

Katherine Kelly Vidal
*Director of the United States Patent and Trademark Office*